United States Patent [19]
Aloisio, Jr. et al.

[11] Patent Number: 5,943,126
[45] Date of Patent: Aug. 24, 1999

[54] METHOD AND APPARATUS FOR DETECTING SURFACE QUALITIES ON AN OPTICAL FIBER

[75] Inventors: Charles J. Aloisio, Jr., Atlanta; Theatrice S. Penn; Leonardo M. Penn, both of Norcross; Tracy E. Brewer, Duluth; Shahabuddin Siddiqui, Lawrenceville, all of Ga.

[73] Assignee: Lucent Technologies Inc., Murray Hill, N.J.

[21] Appl. No.: 09/074,865

[22] Filed: May 8, 1998

Related U.S. Application Data

[63] Continuation-in-part of application No. 08/815,180, Mar. 11, 1997, Pat. No. 5,786,891, and a continuation-in-part of application No. 08/814,673, Mar. 11, 1997, Pat. No. 5,828,448, and a continuation-in-part of application No. 09/015,460, Jan. 29, 1998, Pat. No. 5,880,825.

[51] Int. Cl.$^6$ .................................................... G01N 21/00
[52] U.S. Cl. ........................................ 356/237.1; 356/73.1
[58] Field of Search ............................... 356/73.1, 237.1; 118/665, 670, 668, 672; 427/8–10, 163.2; 65/378, 382, 485, 491; 250/559.42, 559.43, 559.45

[56] References Cited

U.S. PATENT DOCUMENTS

| | | | |
|---|---|---|---|
| 4,021,217 | 5/1977 | Bondybey et al. | 65/13 |
| 4,135,902 | 1/1979 | Oehrie | 65/2 |
| 4,439,467 | 3/1984 | Kassahun et al. | 427/163 |
| 4,988,875 | 1/1991 | Ortiz et al. | 250/330 |
| 5,185,636 | 2/1993 | Button et al. | 356/73.1 |
| 5,208,645 | 5/1993 | Inoue et al. | 356/73.1 |
| 5,228,893 | 7/1993 | Smithgall et al. | 65/2 |
| 5,772,861 | 6/1998 | Meredith, Jr. et al. | 118/665 |

OTHER PUBLICATIONS

Cooling and Bubble–Free Coating of Optical Fibers at a High Drawing Rate, C.M.G. Jochem et al., vol. LT–4, No. 7, Jul., 1986, Journal of Lightwave Technology, pp. 739–742.

*Primary Examiner*—Robert H. Kim
*Assistant Examiner*—Amanda Merlino

[57] ABSTRACT

The present invention provides an optical detection system for detecting surface qualities on an optical fiber. The system comprises a light source for projecting a beam of light onto the outer surface of an optical fiber. An optical detector positioned adjacent the optical fiber receives light reflected from the outer surface of the optical fiber and generates an electrical output signal which is delivered to a signal processing device. The signal processing device analyzes the electrical output signal to determine whether one or more surface qualities exist on the outer surface of the optical fiber. In accordance with the preferred embodiment of the present invention, the optical detection system is used to detect surface qualities that include ink skips, i.e., locations on the outer surface of the optical fiber that do not contain any ink. The signal processing device comprises a computer that records the intensity of the light received by the optical detector array, which corresponds to the magnitude of the electrical signal generated by the optical detector array, along with the location along the optical fiber that corresponds to the electrical output signal. This data can be used by the computer to determine the amount of ink existing at a particular location on the optical fiber, the size and location of an ink skip and the opacity of the ink.

18 Claims, 9 Drawing Sheets

INK SKIP ON COLORED FIBER

METHOD AND APPARATUS FOR DETECTING SURFACE QUALITIES ON AN OPTICAL FIBER

CROSS-REFERENCE TO RELATED APPLICATIONS

The present application is a continuation-in-part application of Ser. No. 08/815,180, filed Mar. 11, 1997, now U.S. Pat. No. 5,786,891, and is a continuation-in-part application of Ser. No. 08/814,673, filed on Mar. 11, 1997, now U.S. Pat. No. 5,828,448, and is a continuation-in-part application of Ser. No. 09/015,460, filed Jan. 29, 1998, now U.S. Pat. No. 5,880,825. All of these related applications are incorporated by reference herein in their entirety.

TECHNICAL FIELD OF THE INVENTION

The present invention relates to a method and apparatus for detecting surface qualities or characteristics on an optical fiber and, more particularly, to a detection system that can be incorporated into an optical fiber manufacturing process for optically detecting surface characteristics, such as, for example, the color and thickness of the outer surface of the optical fiber, as it is being manufactured.

BACKGROUND OF THE INVENTION

The successful implementation of a light wave communication system requires high quality light guide fibers having mechanical properties sufficient to withstand the stresses to which they are subjected. Each fiber must be capable of withstanding over its entire length a maximum stress level to which the fiber will be exposed during installation and service. The importance of fiber strength becomes apparent when one considers that a single fiber failure will result in the loss of several hundreds of circuits.

The failure of light guide fibers in tension is commonly associated with surface flaws which cause stress concentrations and lower the tensile strength below that of pristine unflawed glass. The size of the flaw determines the level of stress concentration and, hence, the failure stress. Even micron-sized surface flaws cause stress concentrations which significantly reduce the tensile strength of the fibers.

Optical fibers are normally made in a continuous process which involves drawing a thin glass strand of fiber from a partially molten glass preform and thereafter applying the coating layers. A furnace is used to partially melt the preform to permit the fiber to be drawn. The heat of the furnace and the rate of draw of the fiber must be in proper balance so that the optical fiber can be drawn continuously under uniform conditions. Long lengths of light guide fibers have considerable potential strength, but the strength is diminished by airlines or holes occurring in the optical fibers. Furthermore, airlines in optical fibers also interfere with the light-propagation properties of the optical fibers.

Soon after an optical fiber is drawn, the optical fiber is coated with a layer of a coating material such as, for example, a polymer. This coating serves to prevent airborne particles from impinging upon and adhering to the surface of the drawn fiber, which would weaken it or even affect its transmission properties. Also, the coating shields the fibers from surface abrasion, which could occur as a result of subsequent manufacturing processes and handling during installation. The coating also provides protection from corrosive environments and spaces the fibers in cable structures. The above-referenced co-pending related applications, Ser. Nos. 08/815,180 and 08/814,673, which are incorporated herein by reference, are directed to detecting defects in an optical fiber coating and detecting and distinguishing between defects in an optical fiber coating, respectively.

It is generally known in the industry to monitor optical fibers as they are being drawn during the manufacturing process to determine whether defects exist in the optical fibers. However, the known techniques analyze the optical fibers during the drawing process before the coating layers have been applied and do not analyze the outer surface of the coated fiber to detect characteristics or qualities relating to the outer surface of the outer coating.

For example, Bondybey et al., U.S. Pat. No. 4,021,217, disclose a system for detecting optical fiber defects to determine the tensile strength of optical fibers as they are being manufactured prior to any coating layers being applied to the optical fiber. The apparatus disclosed in the Bondybey et al. patent projects a focused beam of monochromatic light onto an optical fiber as it is being drawn. A photodetector, such as a photomultiplier, is positioned off axis with respect to the direction in which the light is projected onto the optical fiber so that it receives only scattered light unique to defects contained in the fiber. The output of the detector is received by an electrometer strip chart recorder which plots a scattering trace corresponding to the light detected. The peaks in the scattering trace correspond to defects in the optical fiber.

Button et al., U.S. Pat. No. 5,185,636, disclose a method for detecting defects such as holes in a fiber. The apparatus disclosed in the Button et al patent utilizes a laser for projecting a beam of light onto the optical fiber. Two optical detectors are positioned on each side of the optical fiber. As a result of the coherence and monochromaticity of the laser beam, interference patterns are created in the far field which are detected by the optical detectors. Holes contained in the optical fiber result in fewer fringes in the interference patterns created in the far field. A plurality of light sources are used in order to ensure that light passes through the entire fiber so that no blind spots exist. This is intended to ensure that light will be reflected off of holes contained at any location within the optical fiber and thus will be detected by the optical detectors. Spatial frequency spectra are generated based on the output of the light detectors and the spectra are analyzed to determine whether a hole exists in the optical fiber.

The systems disclosed in Button et al. and Bondybey et al. both perform optical detection of defects in an optical fiber before any coating layers have been applied to the optical fiber. Therefore, these systems do not detect surface characteristics or qualities in the outer surface of a coated optical fiber. The above-referenced co-pending related application having Ser. No. 09/015,460, which is incorporated herein by reference, is directed to detecting defects inside of the optical fiber itself.

In the optical fiber industry, it is common to apply a layer of ink to the outer coating layer of the optical fiber cable. Different color inks are applied to different optical fibers to allow a technician to distinguish between different optical fibers, such as, for example, a transmitting optical fiber and a receiving optical fiber. A well known industry standard defines the colors that are used for different optical fibers in order to distinguish between them However, the coated optical fiber is typically covered with a strength member and a portion of the strength member must be removed in order to ascertain the color of the ink applied to the outer coating layer. Normally, the technician looks at the end of the optical fiber cable to determine the color of the ink applied to the outer coating layer. The technician may be required to remove a portion of the strength member to ascertain the color of the ink applied to the outer coating layer.

A problem sometimes encountered by the technician is that a break in the ink applied to the outer coating layer has occurred, thus making it difficult or impossible for the technician to ascertain the color of the ink. When this happens, the technician may be unable to distinguish between different optical fibers. It is also known that breaks in the ink, sometimes referred to as ink skips, can produce added optical loss. This can occur if the spatial frequency of a skip is located in a critical region for micro-bending.

Accordingly, a need exists for a system for detecting qualities or characteristics in the outer surface of coated optical fibers, such as, for example, a break or inconsistency in the ink layer applied to the outer coating layer of the optical fiber.

SUMMARY OF THE INVENTION

The present invention provides an optical detection system for detecting surface qualities on an optical fiber and, preferably, on a moving optical fiber during the optical fiber manufacturing process. The system comprises a light source for projecting a beam of light onto the coating layer of an optical fiber and an optical detector array that receives the light and converts the light into an electrical output signal. The electrical output signal preferably is amplified and then is converted into a digital signal and input to a computer. The computer compares the received digital signal with a threshold level to determine the type and/or size and/or location of the surface quality. The computer is programmed with detection software which performs the comparison of the received digital signal with the threshold level to analyze the surface quality.

In accordance with the preferred embodiment of the present invention, the optical detection system is used to detect breaks in the ink layer applied to the outer coating layer of the optical fiber. However, it will be apparent to those skilled in the art that the system of the present invention may also be used for detecting other types of surface qualities on the outer surface of the optical fiber. In accordance with the preferred embodiment of the present invention, the computer, under the control of the detection software, generates a baseline voltage from an area of the optical fiber having normal or acceptable surface qualities. For example, if the system is set up to detect breaks in the ink layer applied to the optical fiber, the computer will generate a baseline voltage based on an area of the optical fiber where there are no breaks in the ink. This baseline voltage corresponds to the threshold level that is compared with the digital signal received by the computer. Preferably, the computer compares the digital signal with the threshold level to obtain an absolute value measurement of the difference in magnitude between the threshold level and the digital signal. The computer then utilizes this absolute value to determine the type and/or size and/or location of the surface quality, e.g., of the break in the ink.

Preferably, the computer performs the threshold comparison in real time as the optical fiber is being manufactured. Therefore, the optical fiber is moving as the measurements are being taken. The computer generates a file as the measurements are taken which preferably comprises an indication of the intensity of the signal along with the location on the optical fiber to which the intensity indication corresponds. This saved data preferably is then used to generate a graph relating to the intensity of the particular surface characteristic measurement obtained. This data can then be used to determine the length or size of the surface characteristic and, in the case of ink skips, the measurements taken can be used to determine the opacity of the ink.

When a particular surface characteristic, such as an ink skip, has been detected, the manufacturing process may be altered to prevent additional occurrences of the surface characteristic and/or the optical fiber portion containing the surface characteristic can be discarded. In the case of ink skips, the fiber coloring process, which involves application of ink, can be altered or corrected to prevent further ink skips from occurring. Also, when a particular surface quality, such as an ink skip, for example, has been detected, preferably an audio and/or visual indication is provided to alert the operator.

DETAILED DESCRIPTON OF THE INVENTION

Figure 1:
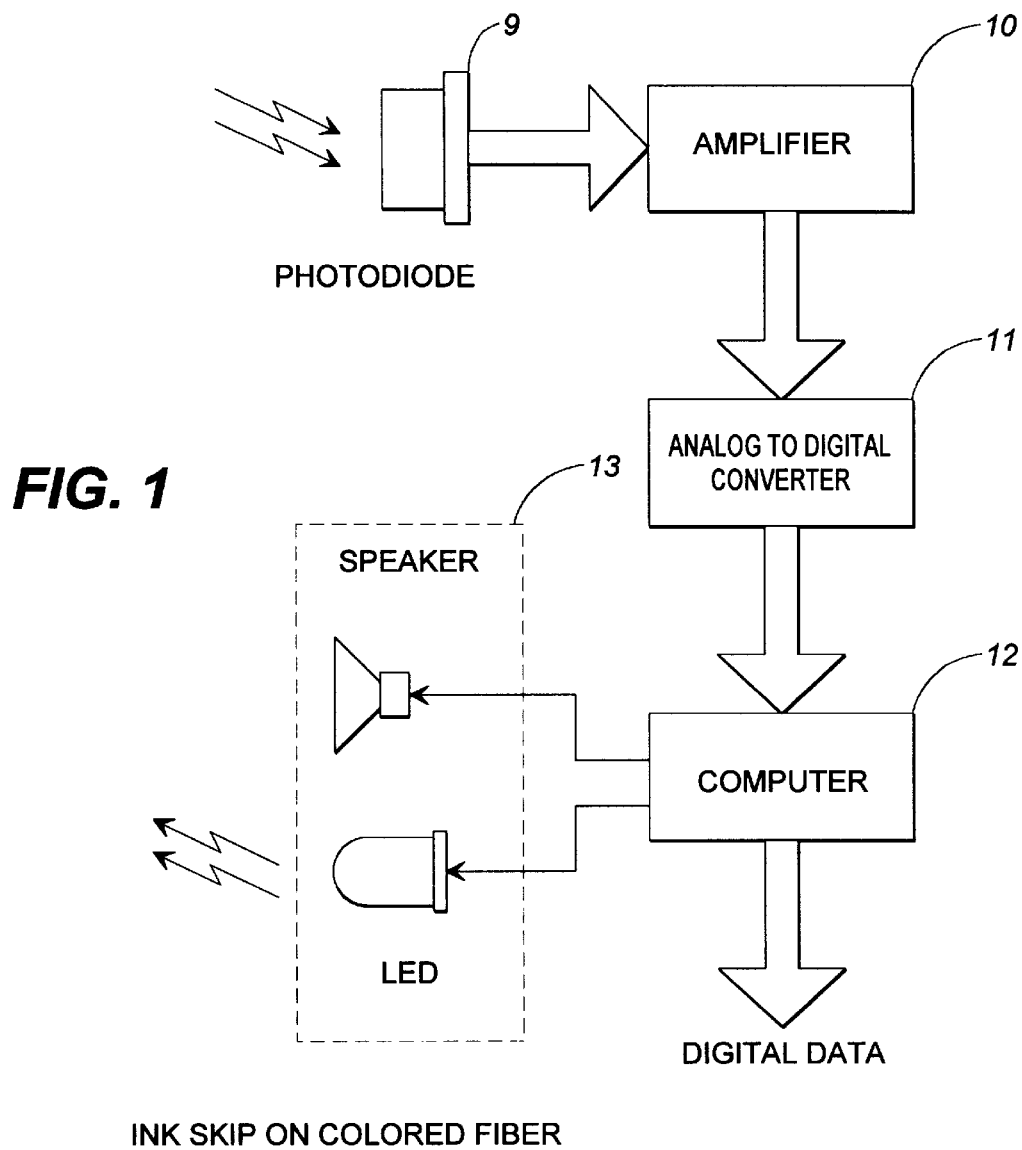
FIG. 1 is a block diagram of the apparatus of the present invention for detecting surface qualities in optical fibers in accordance with the preferred embodiment.

FIG. 1 illustrates the preferred embodiment of the optical detection apparatus 1 of the present invention for detecting defects in an optical fiber. The apparatus 1 of the present invention comprises a light source 7, which preferably is a laser, a lens system 8, an optical detector array 9, which preferably is a linear photosensor array, an amplifier 10 for amplifying the electrical signal generated by the optical detector array 9, an analog-to-digital converter (ADC) 11, a computer 12 and audio and/or visual indicators 13. The ADC 11 and the computer 12 together comprise a signal processing device for processing the detection signal. It will be understood by those skilled in the art, in view of the discussion provided herein, that a variety of signal processing devices can be used with the present invention and that the invention is not limited to any particular signal processing device. It should also be noted that peripheral devices such as a printer and a display terminal, for example, can be interfaced to the signal processing equipment if so desired.

Figure 2:
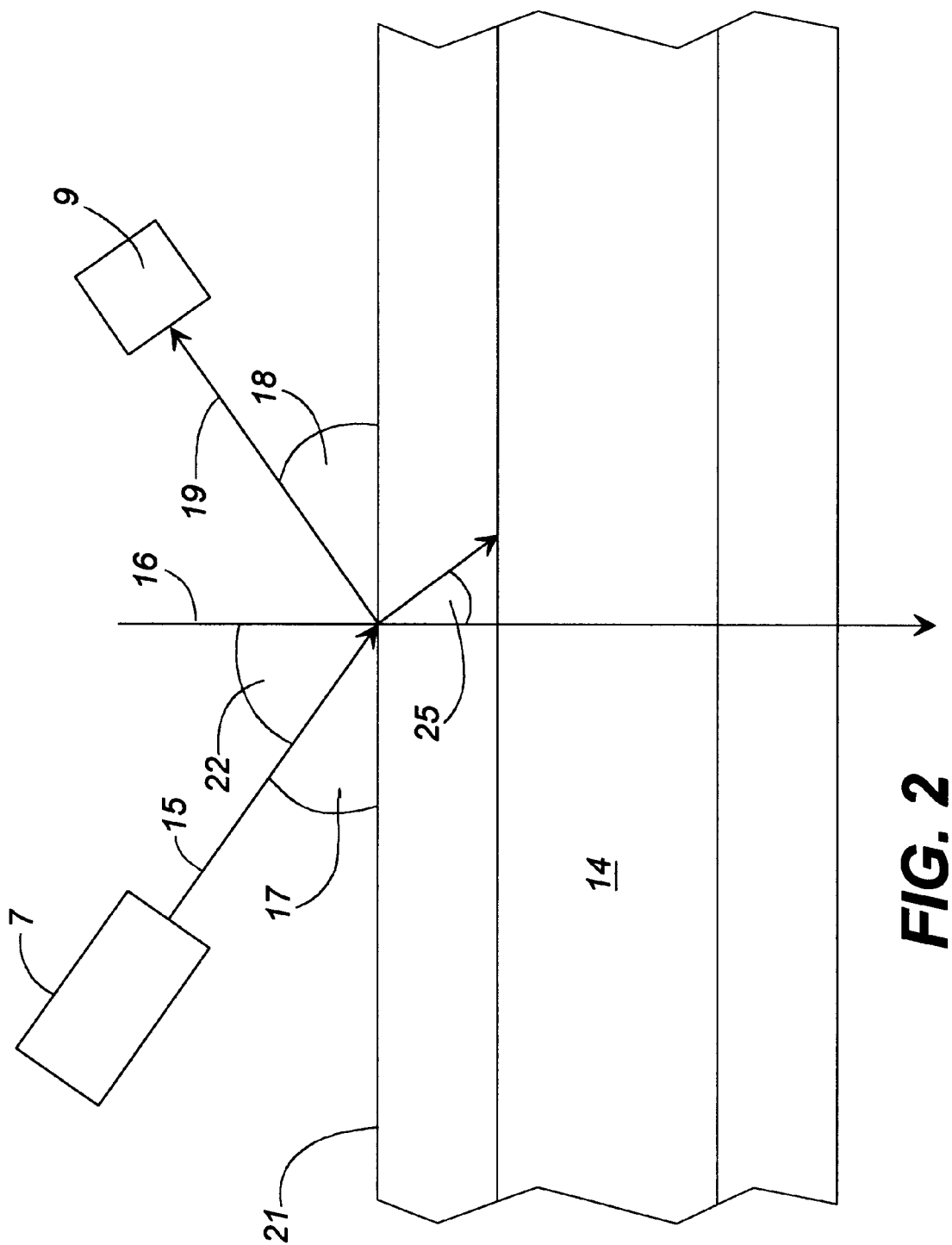
FIG. 2 is a block diagram of the apparatus of the present invention which illustrates the location of the components of the optical detection system of the present invention in relation to a moving optical fiber.

FIG. 2 illustrates the optical detection apparatus 1 shown in FIG. 1 in relation to a moving optical fiber 14. As shown in FIG. 2, a beam of light 15 is projected by laser 7 onto the optical fiber 14 at an angle 22 with respect to a normal 16 to the optical fiber 14. The angle of incidence 17 of the projected light onto the optical fiber 15 preferably is in the range of approximately 5° to approximately 30°. The optical detector array 9 preferably is positioned opposite the optical detector array 9 and at an angle 18 of between approximately 5° and approximately 30° with respect to the longitudinal axis of the optical fiber 14 to receive light 19 reflected from the outer surface 21 of the optical fiber 14. However, it will be understood by those skilled in the art that the present invention is not limited to any particular positions of the laser 7 and/or of the optical detector array 9. These components are merely positioned to achieve the best results. The positions of these components may be adjusted during a calibration sequence to obtain the best detection results. The angle 17 at which the laser 7 projects the beam of light 15 onto the optical fiber 14 should be shallow enough to cause most or all of the light projected onto the optical fiber 14 to be reflected by the surface of the optical fiber 14.

The relationship between the angle of projection 17 and the index of refraction of the outer surface 21 of the optical fiber 14, which will be an ink layer in most cases, can be calculated using the well known law of refraction, also known as Snell's Law. Snell's Law is stated as: $\sin \theta_1 / \sin \theta_2 = n_2/n_1$, where $\theta_1$ is the angle 22 between the normal 16 to the outer surface 21 and the beam of light 15 projected onto the outer surface, $\theta_2$ is the angle 25 between the refracted ray and the normal below the outer surface 21, $n_1$ is the refractive index of air ($\approx 1.0$), and $n_2$ is the refractive index of the outer surface 21 ( e.g., $\approx 1.5-1.7$ for ink). Since it is desirable to cause all of the light 15 projected onto the outer surface 21 of the optical fiber 14 to be reflected, $\theta_1$ must be increased until $\theta_2$ is greater than 90°, i.e., until all of the light projected onto the surface of the optical fiber 14 is reflected by the outer surface 21. Since the indices of refraction of air and of the outer surface 21 are known, the angle $\theta_1$ can be easily calculated to cause total reflection. The angle 18 of the light reflected by the outer surface 21 with respect to the normal to the outer surface 21 is equal to the angle 17 of incidence of the light onto the outer surface 21. Therefore, once $\theta_1$. has been calculated, the angle 17 of incidence, and thus the angle of reflection 18, can be calculated by subtracting $\theta_1$ from 90°.

Therefore, for best detection results, the optical detector array 9 should be positioned at the same angle with respect to the normal to the surface that the laser 7 is positioned at and should be positioned opposite the laser 7 so that most or all of the light reflected from the surface 21 of the optical fiber 14 is received by the array 9. By causing all of the light projected onto the surface 21 to be reflected, the possibility of the detector array 9 receiving light reflected by defects within the optical fiber is substantially reduced or eliminated. However, it will be understood by those skilled in the art that even if the laser 7 is not positioned at an angle that results in total reflection and some of the light from the laser passes into the outer surface 21 and/or into the optical fiber 14, this will not necessarily result in the detector array 9 receiving light reflected from within the outer surface 21 or from within the optical fiber 14 because any such reflections will likely be weak compared to the reflections from the outer surface 21 and therefore can be filtered out by utilizing appropriate filtering circuitry, as will be understood by those skilled in the art.

It should also be noted that the present invention is not limited with respect to the types of components implemented by the optical detection apparatus 1. For example, although the light source 7 preferably is a continuous, infrared laser having an 830 nanometer wavelength, those skilled in the art will understand that the present invention is not limited to this type of light source. Similarly, the present invention is not limited with respect to the type of optical detector 9 utilized with the present invention, or with respect to the computer 12 used for processing the signals received from the optical detector.

Figure 4:
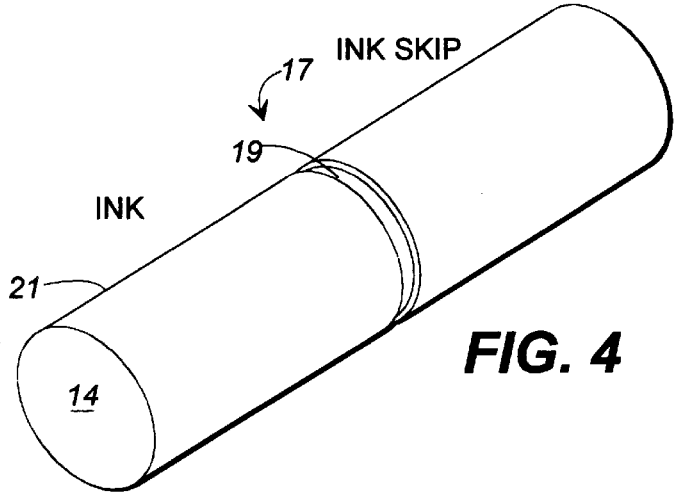
FIG. 4 is a perspective view of a section of an optical fiber having an ink skip on the surface thereof.
Figure 3:
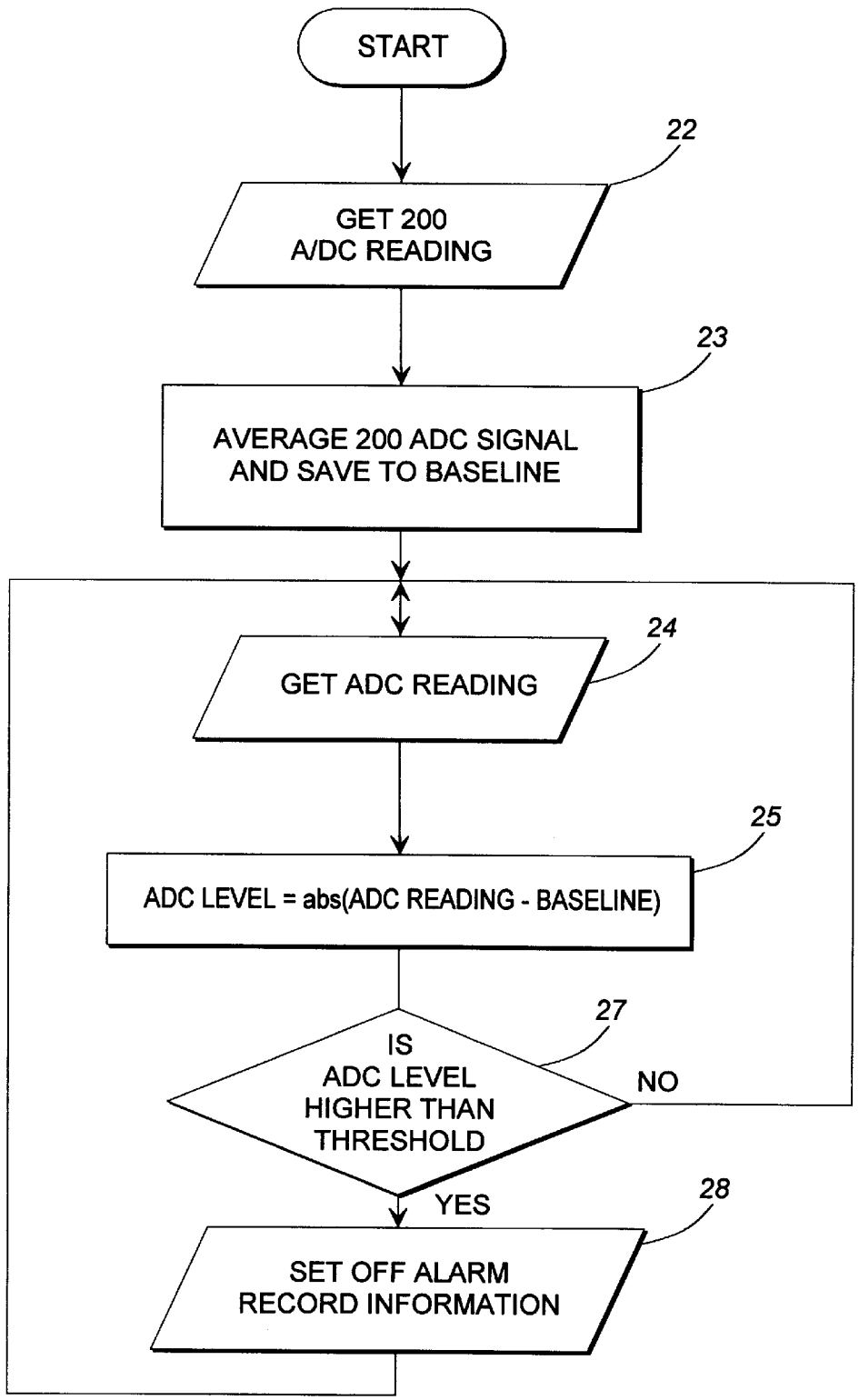
FIG. 3 is a flow chart demonstrating the functionality of the detection software being run on the computer shown in FIG. 1.

FIG. 3 is a flow chart demonstrating the functionality of the detection software being run on the computer 12 shown in FIG. 1. As stated above, in accordance with the preferred embodiment of the present invention, the optical detection system 1 is used to detect breaks in the ink layer applied to the outer coating layer of the optical fiber 14. FIG. 4 is a perspective view of a section 17 of optical fiber 14 having an ink skip 19 on the surface 21 thereof However, it will be apparent to those skilled in the art that the system of the present invention may also be used for detecting other types of surface qualities on the outer surface 21 of the optical fiber.

In accordance with the preferred embodiment of the present invention, the computer 12, under the control of the detection software, generates a baseline voltage from an area of the optical fiber having normal or acceptable surface qualities. For example, if the system is set up to detect breaks in the ink layer applied to the optical fiber, such as ink skip 19, the computer 12 will generate a baseline voltage based on an area of the optical fiber 14 where there are no breaks in the ink. This is indicated in blocks 22 and 23 of FIG. 3. Preferably, a plurality of samples are acquired by the ADC 11 over a predetermined period of time while the optical fiber 14 is moving. Through experimentation, it was determined that 200 readings are sufficient for this purpose. The readings are taken from an area of the optical fiber where there are no ink skips. As indicated in block 23, the readings are then averaged together to obtain a baseline value, which is saved in memory.

It should be noted that different color inks will have different light-absorbing or fight-reflecting characteristics. Whenever light is projected onto an optical fiber, whatever light is not reflected by the optical fiber will be absorbed. Therefore, since optical fibers may have different color inks applied to them, a baseline voltage should be generated for each optical fiber having a particular color ink thereon.

Once the baseline value has been obtained, it is compared with the digital signal received by the computer 12 from the ADC 11 as readings are continuously taken, as indicated in blocks 24 and 25. When the digital detection signal is either greater than or less than the baseline voltage by a predetermined amount, the software determines that a particular surface quality, such as an ink skip, for example, has been detected. This is indicated in block 27, which indicates that a comparison is made between the reading from the ADC 11 and the baseline value to obtain an "ADC level" signal. Preferably, the computer 12 compares the "ADC level" signal with a threshold level to determine whether a particular surface quality, such as an ink skip, for example, has been detected. Preferably, an alarm is set off when the ADC level obtained in step 27 is higher than the threshold level, as indicated by block 28. The computer 12 preferably utilizes these measurements to determine the type and/or size and/or location of the surface quality, e.g., of the break in the ink.

Preferably, the computer 12 performs the comparisons in real time as the optical fiber 14 is being manufactured. Therefore, the optical fiber 14 is moving as the measurements are being taken. The computer 12 generates a file as the measurements are taken which preferably comprises an indication of the intensity of the signal along with the location on the optical fiber 14 to which the intensity indication corresponds. This file is stored in a memory device (not shown) which may be within the computer 12 or external to the computer 12. This saved data preferably is then used to generate a graph relating to the density of the particular surface characteristic measurement obtained. This data can then be used to determine the length or size of the surface characteristic and, in the case of ink skips, the measurements taken can be used to determine the opacity of the ink.

Figure 5:
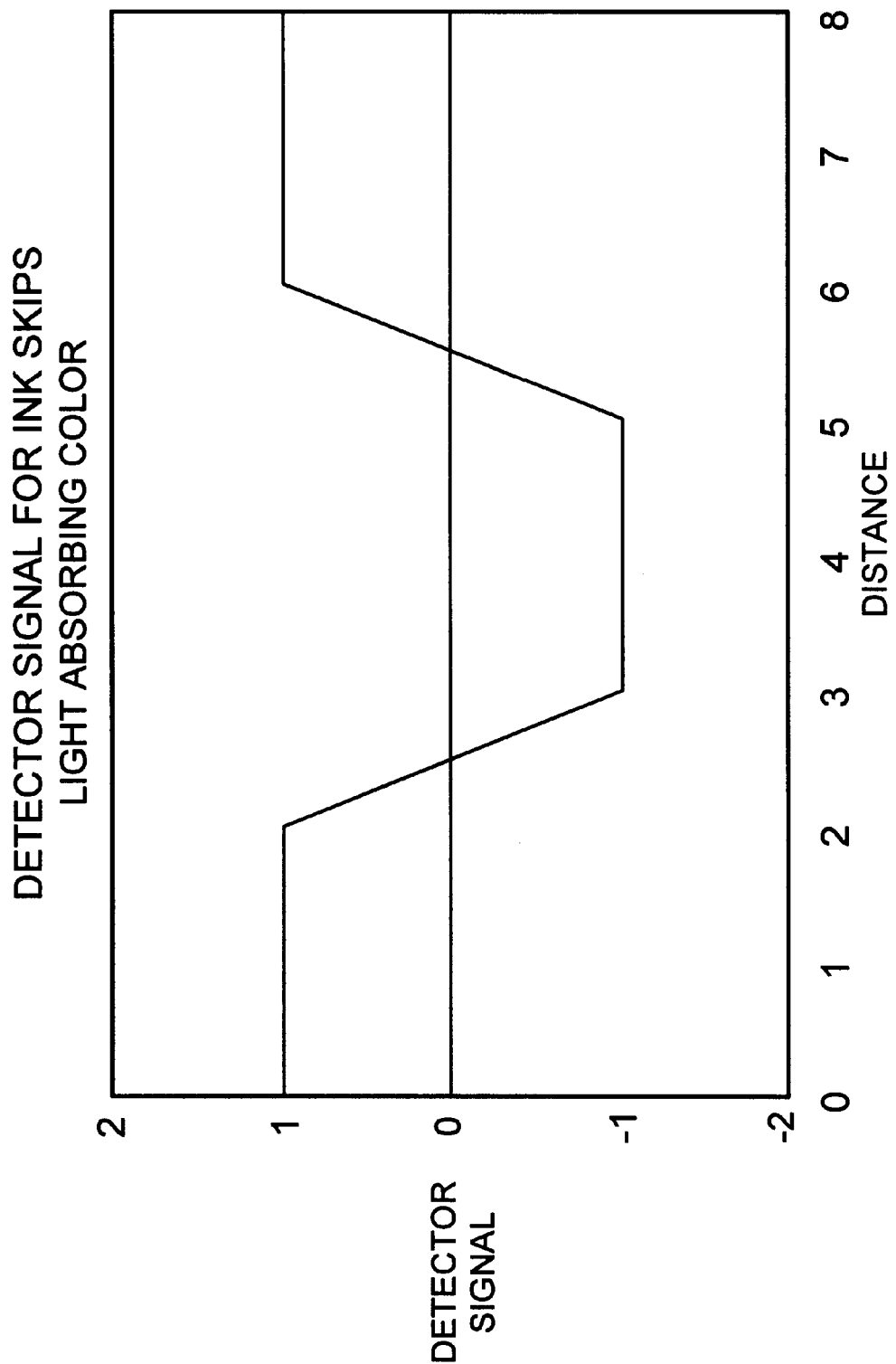
FIG. 5 is a graph demonstrating the magnitude of the detection signal received by the computer shown in FIG. 1 in relation to the position of the optical fiber wherein the ink on the surface of the optical fiber has a light-absorbing color.

FIG. 5 is a graph demonstrating the magnitude of the detection signal received by the computer 12 in relation to the position of the optical fiber 14 along the manufacturing line (not shown). The graph shown in FIG. 5 relates to an optical fiber covered with ink that has a light-absorbing color. The magnitudes of the detector signal shown on the vertical axis have been chosen as ranging between 1– and +1 for simplicity and for the purpose of demonstrating the concepts of the present invention. In this particular example, the detector signal, which corresponds to the "ADC level" in block 27 of FIG. 3, begins dropping below the baseline voltage of 1 at a particular location along the fiber and remains below the baseline voltage level for approximately 4 meters. The detector signal is at –1 for approximately 2 meters of fiber. The threshold value will be chosen to be somewhere between the baseline value and the value of the detector signal when there is no ink on the fiber.

Figure 6:
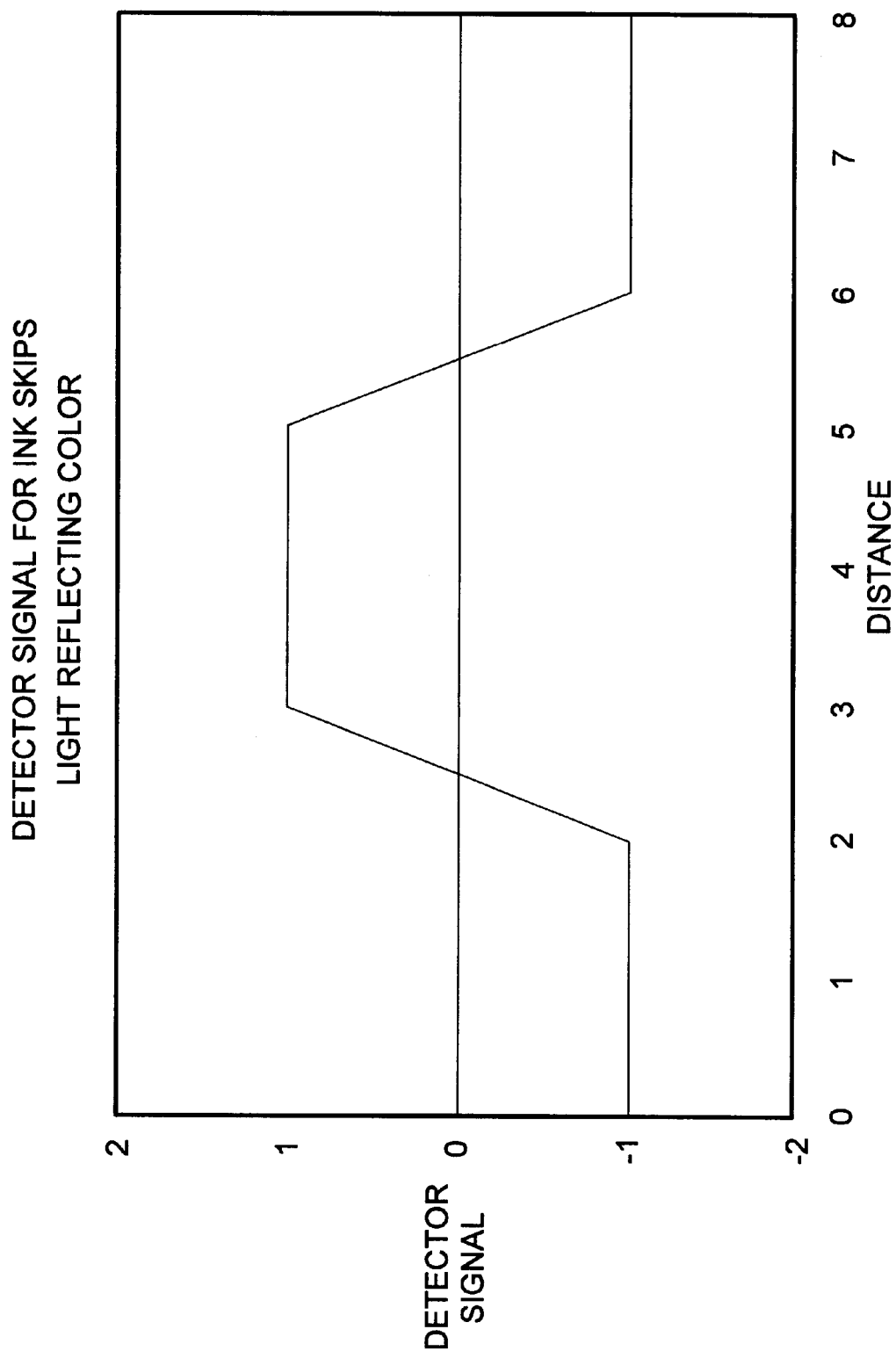
FIG. 6 is a graph demonstrating the magnitude of the detection signal received by the computer shown in FIG. 1 in relation to the position of the optical fiber with respect to the optical detection system wherein the ink on the surface of the optical fiber has a light-reflecting color.

FIG. 6 is a graph demonstrating the magnitude of the detection signal received by the computer 12 wherein the ink on the surface of the optical fiber has a light-reflecting color. The baseline voltage generated from the section of fiber not containing the ink skip is –1. When the ink skip occurs, the detector signal increases above the baseline voltage and remains above the baseline voltage for approximately 4 meters. The detector signal is at +1 for approximately 2 meters of fiber, which indicates that the detector signal corresponds to an ink skip. Preferably, the threshold level is chosen so that it does not have to be changed to one value for ink having a light-absorbing color and to another value for ink having a light-reflective color. In accordance with the preferred embodiment, the ADC 11 generates an output signal ranging in digital value from 34 to 255, with 255 corresponding to a complete absence of ink on the fiber and 34 corresponding to the baseline value. Preferably, the threshold value is approximately 50, which has been determine through experimentation to be a suitable value for use with light-absorbing ink and light-reflecting ink.

As stated above, the software generates a file which comprises data relating to the location along the fiber at which an ink skip occurred. The software also preferably generates a file which comprises data relating to the intensity of the digital detection signal and the location along the fiber at which each intensity measurement was acquired. This intensity data can be used to determine the ink opacity at any location along the fiber. Furthermore, the intensity and size of the measured surface feature can be used to determine the type of surface quality detected. As stated above, once a particular surface quality has been detected, the computer 12 preferably causes an audio and/or visual indication to be provided to the operator to alert the operator that a particular surface feature has been detected, as indicated by block 28 in FIG. 3.

Figure 7:
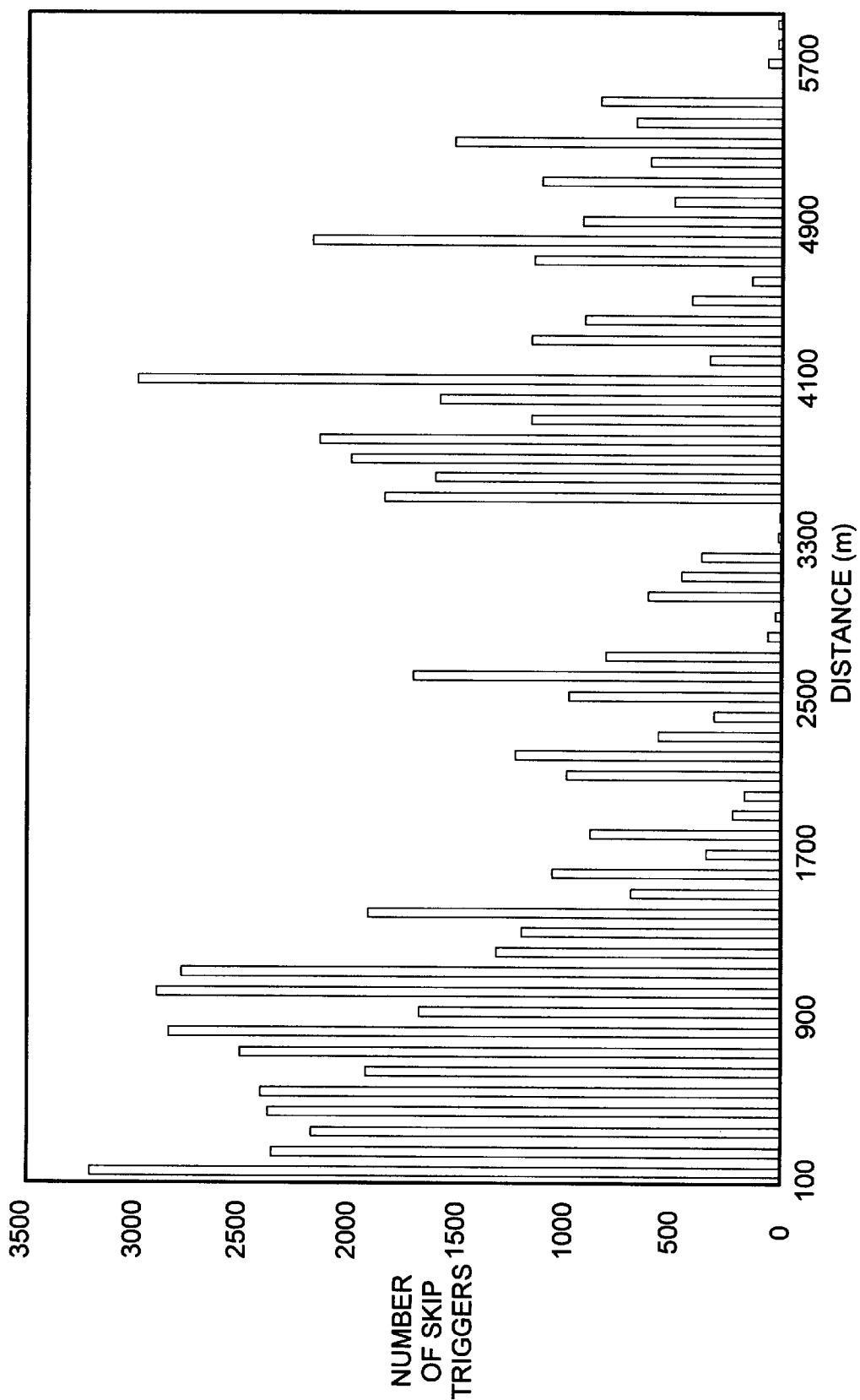
FIG. 7 is a graph demonstrating the density of ink skips on an optical fiber in relation to the position of the optical fiber with respect to the optical detection system wherein brown ink has been applied to the optical fiber.

FIG. 7 is a graph demonstrating the density of ink skips detected every 100 meters along an optical fiber. This type of graph is generated using the data corresponding to the intensity of the detection signal at locations along the optical fiber. This information can be used to determine whether a particular length of fiber should be discarded, and/or to determine where an optical fiber is to be severed so that the end of the optical fiber does not contain an ink skip or some other surface quality which is undesired at that particular location.

Figure 8:
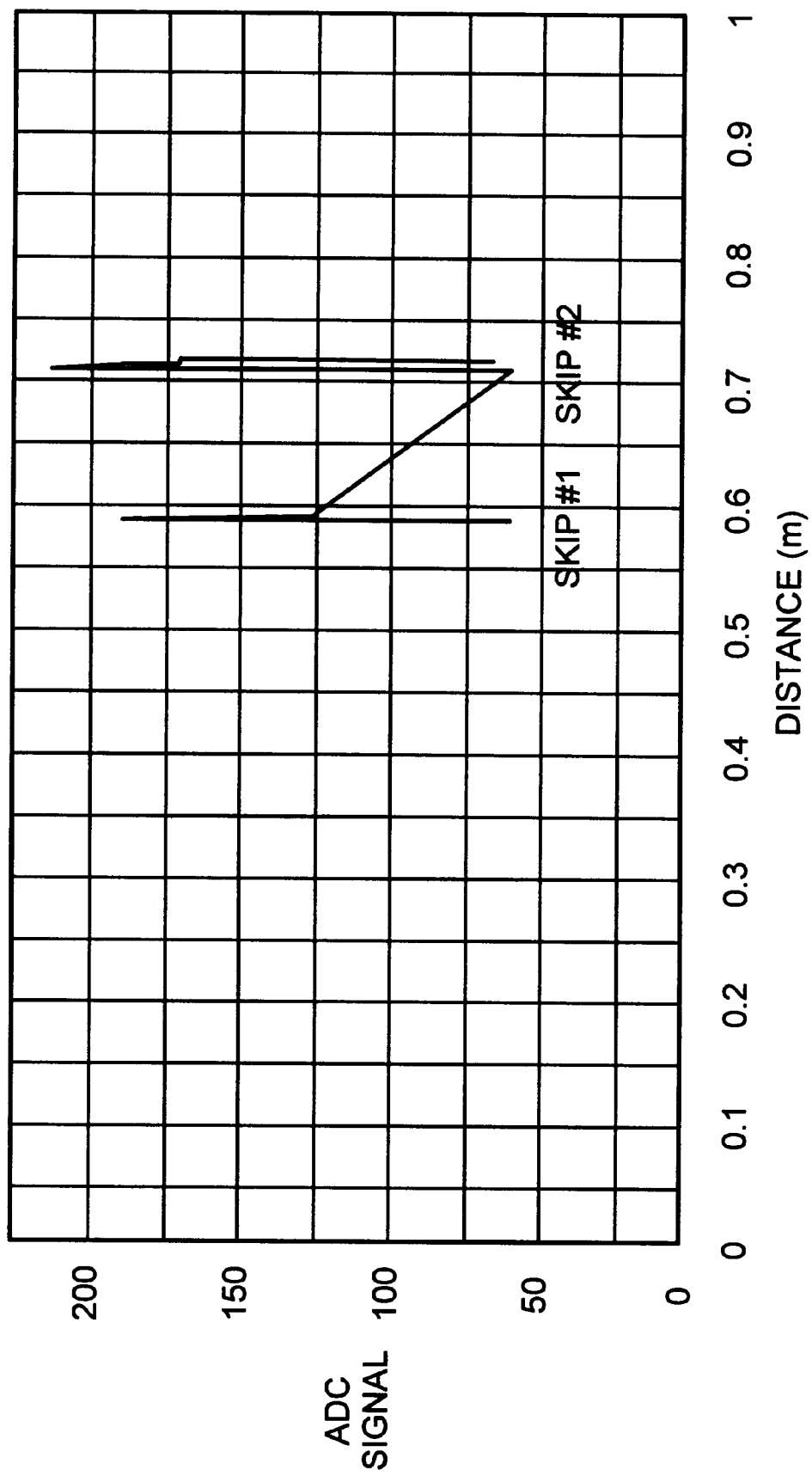
FIG. 8 is a graph demonstrating the magnitudes of the digital detection signals received by the computer shown in FIG. 1 in relation to the position of the optical fiber with respect to the optical detection system wherein two ink skips have been detected.
Figure 9:
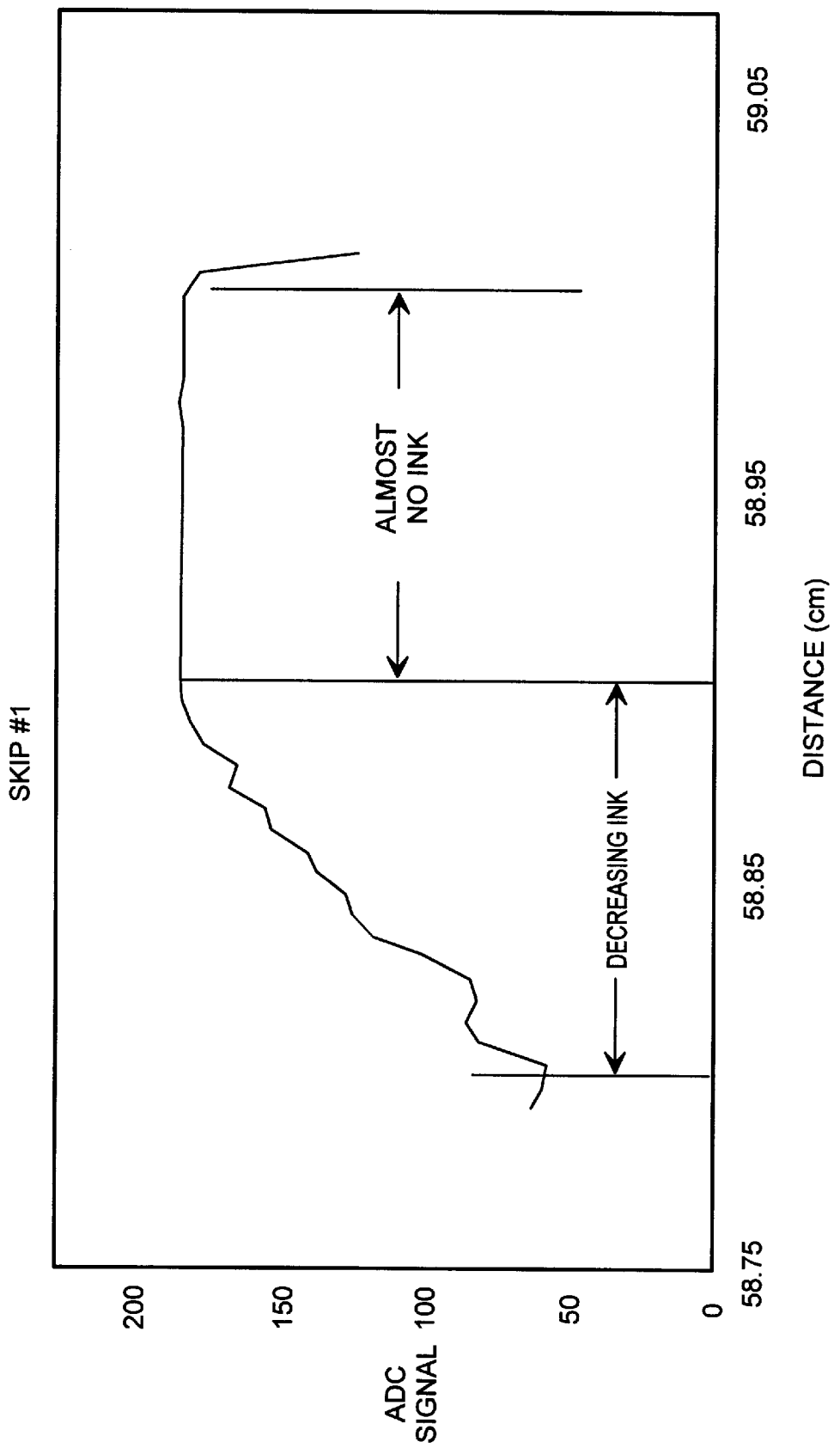
FIGS. 9 and 10 are expanded views of the graph shown in FIG. 8, each of which shows a close up view of one of the two ink skips shown in FIG. 8.
Figure 10:
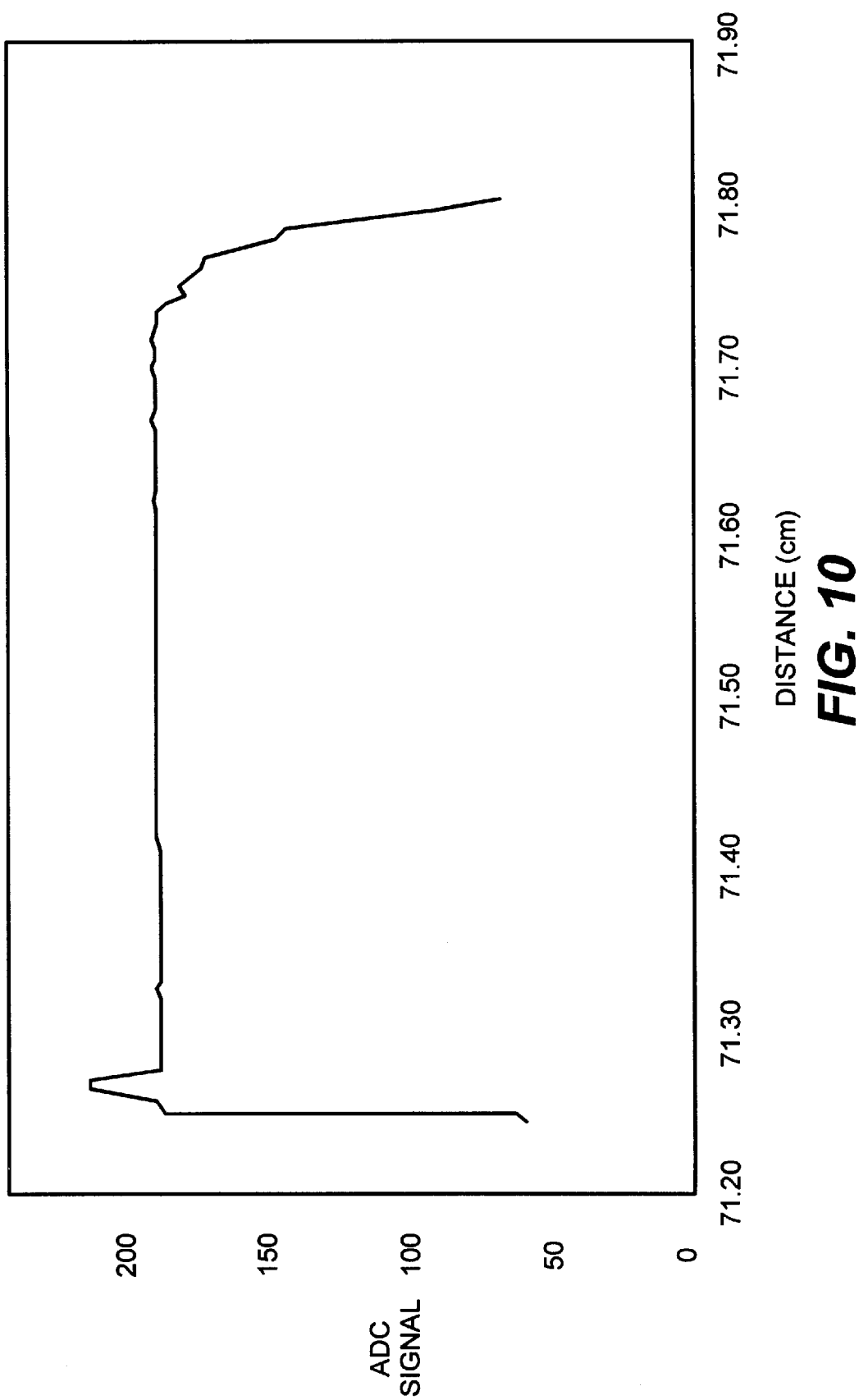

FIG. 8 is a graph demonstrating the magnitudes of the digital detection signals received by the computer 12 in relation to the position of the optical fiber with respect to the optical detection system wherein two ink skips, skip #1 and skip #2, have been detected. In this experiment, the ink contained on the optical fiber was orange in color. These ink skips are only approximately 0.1 meters apart from each other. FIGS. 9 and 10 are expanded views of the graph shown in FIG. 8, each of which shows a close up view of one of the two ink skips shown in FIG. 8. It can be seen in FIG. 9 that the detection signal increases as the amount of ink on the fiber decreases. The detection signal reaches a constant value where almost no ink exists on the fiber. The digital detection signal from the ADC 11 is in millivolts in this experiment.

In FIG. 9, ink skip #2 corresponds to a portion of the fiber that is completely devoid of ink and a larger portion of the fiber that has almost no ink on it. Where no ink exists, the detection signal increases quickly until it reaches a maximum value in excess of 200 millivolts. The detection signal then decreases to slightly less than 200 millivolts where it remains constant for approximately 0.4 centimeters. The detection signal then decreases to approximately 60 millivolts as more ink begins being detected.

It will be understood by those skilled in the art that although the present invention has been discussed primarily with respect to detecting the precise locations and sizes of ink skips on an optical fiber, the detection system of the present invention can also be used for detecting other types of surface qualities. It will be understood by those skilled in the art that modifications may be made to the optical detection system discussed above which are within the scope of the present invention. It should be noted that although the present invention has been described with respect to particular embodiments, the present invention is not limited to these embodiments.

What is claimed is:

1. An apparatus for detecting one or more surface qualities on an outer surface of a coating layer of an optical fiber, the apparatus comprising:

a light source for projecting a beam of light onto the outer surface of the coating layer of the optical fiber;

an optical detector positioned to receive light reflected from the outer surface, the optical detector generating an electrical output signal in response to the light received thereby; and a signal processing device electrically coupled to the optical detector, the signal processing device receiving the electrical output signal from the optical detector and processing the electrical output signal to determine whether the optical detector has detected said one or more surface qualities.

2. An apparatus according to claim 1, wherein the light is projected onto the outer surface of the coating layer of the optical fiber at a relatively shallow angle with respect to a longitudinal axis of the optical fiber, and wherein the optical detector is positioned to receive substantially all of the light reflected by the outer surface.

3. An apparatus according to claim 1, wherein said one or more surface qualities include an ink skip.

4. An apparatus according to claim 3, wherein the signal processing device generates a baseline voltage corresponding to an area on the outer surface of the coating layer of the optical fiber where no ink skips exist and wherein the signal processing device compares the baseline voltage with the electrical output signal to determine a difference between the baseline voltage and the electrical output signal, wherein the signal processing device records the difference and a location at which the electrical output signal corresponding to the difference occurred along the optical fiber.

5. An apparatus according to claim 4, wherein the signal processing device comprises an analog-to-digital converter and a computer, the analog-to-digital converter receiving the electrical output signal from the optical detector and converting the electrical output signal into a digital representation of the electrical output signal, wherein the computer receives the digital representation and processes the digital representation to determine whether an ink skip has been detected and the location along the optical fiber at which the ink skip was detected.

6. An apparatus according to claim 5, wherein each digital representation indicates an intensity value of the electrical output signal and wherein the computer records the intensity values and the location along the optical fiber corresponding to the recorded intensity value, wherein the computer determines ink opacity at locations along the optical fiber from the recorded intensity values.

7. An apparatus according to claim 6, wherein the light source projects light onto the outer surface of the coating layer of the optical fiber at an angle between approximately 5° and approximately 30° with respect to a longitudinal axis of the optical fiber.

8. An apparatus according to claim 4, wherein a baseline voltage is generated for various colors, each of the various colors corresponding to the color of ink on the outer surface of the coating layer of the optical fiber.

9. An apparatus according to claim 5, wherein each digital representation indicates an intensity value of the electrical output signal and wherein the computer records the intensity values and the location along the optical fiber corresponding to the recorded intensity value, wherein the computer determines ink thickness at locations along the optical fiber from the recorded intensity values.

10. A method for detecting one or more surface qualities on an outer surface of a coating layer of an optical fiber, the method comprising the steps of:

projecting light from a light source onto the outer surface of the coating layer of the optical fiber;

receiving light reflected from the outer surface of the coating layer of the optical fiber at an optical detector, the optical detector generating an electrical output signal in response to receiving the reflected light;

receiving the electrical output signal in a signal processing device, the signal processing device analyzing the electrical output signal to determine whether said one or more surface qualities have been detected.

11. The method of claim 10, wherein the light is projected onto the outer surface of the coating layer of the optical fiber at a relatively shallow angle with respect to a longitudinal axis of the optical fiber so that substantially all of the light projected onto the optical fiber is reflected by the outer surface, and wherein the optical detector is positioned to receive substantially all of the light reflected by the outer surface.

12. The method of claim 10, wherein the outer surface comprises a layer of ink and wherein said one or more surface qualities include an ink skip.

13. The method of claim 12, further comprising the step of utilizing the electrical output signal received in the signal processing device to generate a baseline voltage during a calibration sequence, the baseline voltage being generated before the signal processing device determines whether said one or more surface qualities have been detected, the electrical output signal being used for generating the baseline voltage corresponding to an area on the outer surface of the coating layer of the optical fiber where no ink skips exist, and wherein after the calibration sequence has ended, the signal processing device compares the baseline voltage with the electrical output signal to determine a difference between the baseline voltage and the electrical output signal, wherein the signal processing device records the difference and a location at which the electrical output signal corresponding to the difference occurred along the optical fiber.

14. The method of claim 13, wherein the signal processing device comprises an analog-to-digital converter and a computer, the analog-to-digital converter receiving the electrical output signal from the optical detector and converting the electrical output signal into a digital representation of the electrical output signal, wherein the computer receives the digital representation and processes the digital representation to determine whether an ink skip has been detected and the location along the optical fiber at which the ink skip was detected.

15. The method of claim 14, wherein a baseline voltage is generated for various colors, each of the various colors corresponding to the color of ink on the outer surface of the coating layer of the optical fiber.

16. The method of claim 14, wherein each digital representation indicates an intensity value of the electrical output signal and wherein the computer records the intensity values and the location along the optical fiber corresponding to the recorded intensity value, wherein the computer utilizes the recorded intensity values to determine ink opacity at locations along the optical fiber.

17. The method of claim 14, wherein each digital representation indicates an intensity value of the electrical output signal and wherein the computer records the intensity values and the location along the outer surface of the coating layer of the optical fiber corresponding to the recorded intensity value, wherein the computer determines ink thickness at locations along the outer surface of the coating layer of optical fiber from the recorded intensity values.

18. The method of claim 14, wherein the light source projects light onto the outer surface of the coating layer of the optical fiber at an angle between approximately 5° and approximately 30° with respect to a longitudinal axis of the optical fiber.

* * * * *